US00PP20743P2

(12) United States Plant Patent
Kordes

(10) Patent No.: US PP20,743 P2
(45) Date of Patent: Feb. 9, 2010

(54) SHRUB ROSE PLANT NAMED 'KORSINEO'

(50) Latin Name: *Rosa hybrida*
Varietal Denomination: KORsineo

(75) Inventor: Wilhelm Kordes, Klein Offenseth-Sparrieshoop (DE)

(73) Assignee: W. Kordes ' Söhne Rosenschulen GmbH & Co KG

( * ) Notice: Subject to any disclaimer, the term of this patent is extended or adjusted under 35 U.S.C. 154(b) by 0 days.

(21) Appl. No.: 12/228,866

(22) Filed: Aug. 15, 2008

(51) Int. Cl.
*A01H 5/00* (2006.01)

(52) U.S. Cl. ..... Plt./149

(58) Field of Classification Search ..... Plt./149
See application file for complete search history.

(56) References Cited

OTHER PUBLICATIONS

2007/11340, European Union CVPO summary, Jun. 13, 2007, European Union.

*Primary Examiner*—Annette H Para

(57) ABSTRACT

A new and distinct variety of rose with long lasting, novel hot pink flowers, and attractive foliage with good disease resistance. It exhibits bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORsineo'.

BACKGROUND OF TIIE INVENTION

The new variety of rose plant of the present invention originated from a controlled crossing in a breeding program of two distinct parents during the summer of 1998. The crossing was between 'KORmixal' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsineo'.

SUMMARY OF THE INVENTION

The new rose plant may be distinguished from its seed parent, 'KORmixal', by the following combination of characteristics:

1. The flower color of 'KORmixal' is dark red, while the flower color of 'KORsineo' is hot pink.
2. The petal count of 'KORmixal' is single, while the petal count of 'KORsineo' is very double.

The new rose plant may be distinguished from its pollen parent, an 'un-named seedling' by the following combination of characteristics:

1. The foliage size of the 'un-named seedling' is medium, while the foliage size of 'KORsineo' is small.
2. The petal count of the 'un-named seedling' is semi-double, while the petal count of 'KORsineo' is very double.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORsineo' from all other varieties of which we are aware.

As part of a rose development program, Wilhelm Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsineo' was selected in April, 1999 from the seedling beds to be asexually propagated for further evaluation. The first asexual propagation of 'KORsineo' was done by budding to seedling understocks in July, 1999 at the inventor's nursery in Offenseth-Sparrieshoop, Germany.

This initial and other subsequent propagations conducted in controlled environments demonstrate that 'KORsineo' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORsineo'.

Specifically illustrated in SHEET ONE is a stem exhibiting thorns; tight bud and half opened flower bloom; typical stem with flowers; juvenile foliage and tip of stem; dissected receptacle and detached sepal; and leaves.

DETAILED BOTANICAL DESCRIPTION

The following is a description of 'KORsineo', as observed in its growth in July, 2008 in a nursery in Jackson County, Oreg. on plants of three years of age. Color references are made using The Royal Horticultural Society (London, England) Colour Chart, 2001 except where common terms of color are used.

For a comparison, several physical characteristics of the rose variety 'KORsupigel', a rose variety from the same inventor described and illustrated in U.S. Plant patent application Ser. No. 12/008,955 and issued on Jan. 14, 2008 are compared to 'KORsineo' in Chart 1.

CHART 1

| Characteristic | 'KORsinco' | 'KORsupigel' |
|---|---|---|
| Overall height | 60-70 cm | 40-50 cm |
| Petal count | 40-45 | 40-60 |
| Average leaf size | 100-105 mm × 50-60 mm | 75 mm × 50 mm |

Parents:

*Seed parent.*—'KORmixal'.

*Pollen parent.*—An 'un-named seedling'.

Classification:

*Botanical classification.*—*Rosa hybrida,* 'KORsineo'.

*Commercial classification.*—Shrub rose.

FLOWER AND FLOWER BUD

Blooming habit: Recurrent.

*Flower bud.*—Size: Upon opening, 20 mm in length from base of receptacle to end of bud and 15 mm in diameter at its widest point. Bud form: Short and globular. Bud color: As sepals first unfold, bud color is Red-Purple Group N57A. When ¼ open, the upper surface of petals is Red-Purple Group N57A, and the lower surface of petals is Red-Purple Group N57B. Sepals: Size: Average 5–6 mm long×5–6 mm wide. Shape: Sepals generally subulate. Sepal apex is generally cirrose. Weak foliaceous appendages on three of the five sepals. Base is flat at union with receptacle. Quantity: Five. Margins: With stipitate glands on outer surface. Surface texture: Inner side: Covered in long, fine, white hairs. Outer surface: Stipitate glands are present. Color: Upper surface Yellow-Green Group 144B. Lower surface Yellow-Green Group 144B. Intonations: Greyed-Purple Group 185A.

*Receptacle.*—Surface: Smooth. Color: Green Group 143C. Shape: Pear-shaped. Size: 6 mm (h)×4–5 mm (w).

*Peduncle.*—Surface: With stipitate glands. Length: 18–20 mm average length. Diameter: 1 mm average diameter. Color: Yellow-Green Group 144C. Strength: Nodding. Borne: Multiple flower buds per stem, generally 6 to 8. Anthocyanin: Greyed-Purple Group 183A.

Flower bloom:

*Fragrance.*—Light and sweet.

*Duration.*—Long lasting. The blooms have a duration on the plant of approximately 6 to 7 days. Senesced petals drop.

*After opening, petals.*—Outermost petals: Outer Side: Red-Purple Group N57B. Inner Side: Red-Purple Group N57A. Innermost petals: Outer Side: Red-Purple Group N57C. Inner Side: Red-Purple Group N57B.

*After opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1C. Inner Side: Green-Yellow Group 1C. Variegations: None.

General tonality: On open flower Red-Purple Group N57B. No change in the general tonality at the end of the 7th day. Afterwards, general tonality is Red-Purple Group N57C.

Petals:

*Petal count.*—Approximately 40–42 petals under normal conditions.

*Petal reflex.*—Petals reflex slightly.

*Petal edge.*—Entire and smooth.

*Petal shape.*—Obovate. Apex shape is round. Shape of base is round. away cleanly.

*Size.*—Small flowered garden rose. When open, the average flower diameter is 32–34 mm and the average flower height is 15–18 mm.

*Form.*—Shape of flower when viewed from the side: Upon opening, upper part: Flat. Upon opening, lower part: Flattened convex. Open flower, upper part: Convex. Open flower, lower part: Concave.

Color:

*Upon opening, petals.*—Outermost petals: Outer Side: Red-Purple Group N57B. Inner Side: Red-Purple Group N57A. Innermost petals: Outer Side: Red-Purple Group N57B. Inner Side: Red-Purple Group N57A.

*Upon opening, basal petal spots.*—Basal petal spot, outermost petals: Outer Side: Green-Yellow Group 1C. Inner Side: Green-Yellow Group 1C. Basal petal spot, innermost petals: Outer Side: Yellow Group 2C. Inner Side: Yellow Group 2B.

*Petal size.*—15–18 mm long; 12–15 mm wide.

*Thickness.*—Thin.

*Petal arrangement.*—Generally in a regular pattern with overlapping edges.

Petaloids: Present.

*Petaloid count.*—Average of 8–10 per flower.

*Petaloid edge.*—Undulated.

*Petaloid texture.*—Ruffled.

*Petaloid shape.*—Elongated. Entire. Shape of apex is round, shape of base is pointed.

*Petaloid size.*—Petaloids are 7 mm long and 5 mm wide.

*Petaloid color.*—Color of inner side is Red-Purple Group N57A. Color of outer side is Red-Purple Group N57B.

Reproductive organs:

*Pistils.*—Approximately 20–30 present. Stigmas: Location: Slightly inferior in position to anthers. Color: Green-Yellow Group 1B. Styles: Length: 3 mm long. Color: Green-Yellow Group 1D. Intonations of Red-Purple Group 58A.

*Stamens.*—Approximately 20–30 on average and regularly arranged. Anthers: Size: 1.0–1.5 mm long.

Color: Yellow Group 14A. Pollen: Absent. Filaments: Color: Yellow Group 5B. Length: 4 mm.

THE PLANT

*Plant growth.*—Vigorous. Bushy habit. When grown as a budded nursery plant the average plant height is 60–70 cm and the average plant width is 50–60 cm.

*Stems.*—Stem color: Young wood: Yellow-Green Group 144B. Older wood: Yellow-Green Group 146B. Stem surface: Young wood: Smooth. Older wood: Rough.

*Prickles.*—Present. Incidence: 7–9 per 10 cm of stem. Size: Average length: 8 mm. Color: Immature prickles: Greyed-Purple Group 185B. Mature prickles: Greyed-Purple Group 184A. Senescing to Greyed-Orange Group 165C. Shape: Deeply concave. Anthocyanin: Not observed.

*Leaves and leaflets.*—Normally 5–7 leaflets on normal leaves in middle of the stem. Venation pattern: Pyramidal net pattern. Leaf size: 100–105 mm (l)×50–60 mm (w). Quantity: Limited. Texture: Upper side of leaflet: Glossy and smooth. Under side of leaflet: Matte and smooth. Color, mature foliage: Upper Leaf Surface: Green Group 137A. Lower Leaf Surface: Green Group 138B. Color, juvenile foliage: Upper Leaf Surface: Green Group 137A. Lower Leaf Surface: Green Group 138B. Anthocyanin intonation: Absent.

*Stipules.*—Size: 15–20 mm long. 7 mm between the tips of the stipule. Main body of stipule 7 mm in width. Shape: Longitudinally flanged or winged along middle. Stipule color: Yellow-Green Group 144A. Presence of stipitate glands: Present on margins. Margins: Serrated. With stipitate glands and fine, white hairs.

*Petiole.*—Length: 11–13 mm. Diameter: 1.0 mm. Petiole color: Green Group 138A. Underneath: An occasional prickle. Stipitate glands: Not present. Margins: With long white hairs.

*Petiole rachis.*—Length: 8–15 mm. Diameter: 1.0 mm. Color: Green Group 138A. Margins: With long white hairs. Prickles: An occasional prickle underneath. Stipitate glands: Not present. Anthocyanin: Greyed-Red Group 178A.

*Leaflets.*—Size: Average size of the terminal leaflet is 30 mm (l)×18 mm (w). Shape: Ovate. Base: Ovate. Apex: Acute Margins: Finely serrated. Texture: Thin.

Hips/seed formation: None observed.

Winter hardiness: To date, the variety has been grown successfully in Zone 5.

Disease resistance: Above average resistance to powdery mildew, rust, and Black spot disease under normal growing conditions.

I claim:

1. A new and distinct variety of rose plant characterized by the following combination of characteristics:

(a) Forms attractive, long lasting hot pink flowers;

(b) Exhibits bushy growth habit;

(c) Propagates well using traditional methods, and;

(d) Exhibits very good resistance to disease under normal growing conditions, substantially as herein illustrated and described.

* * * * *

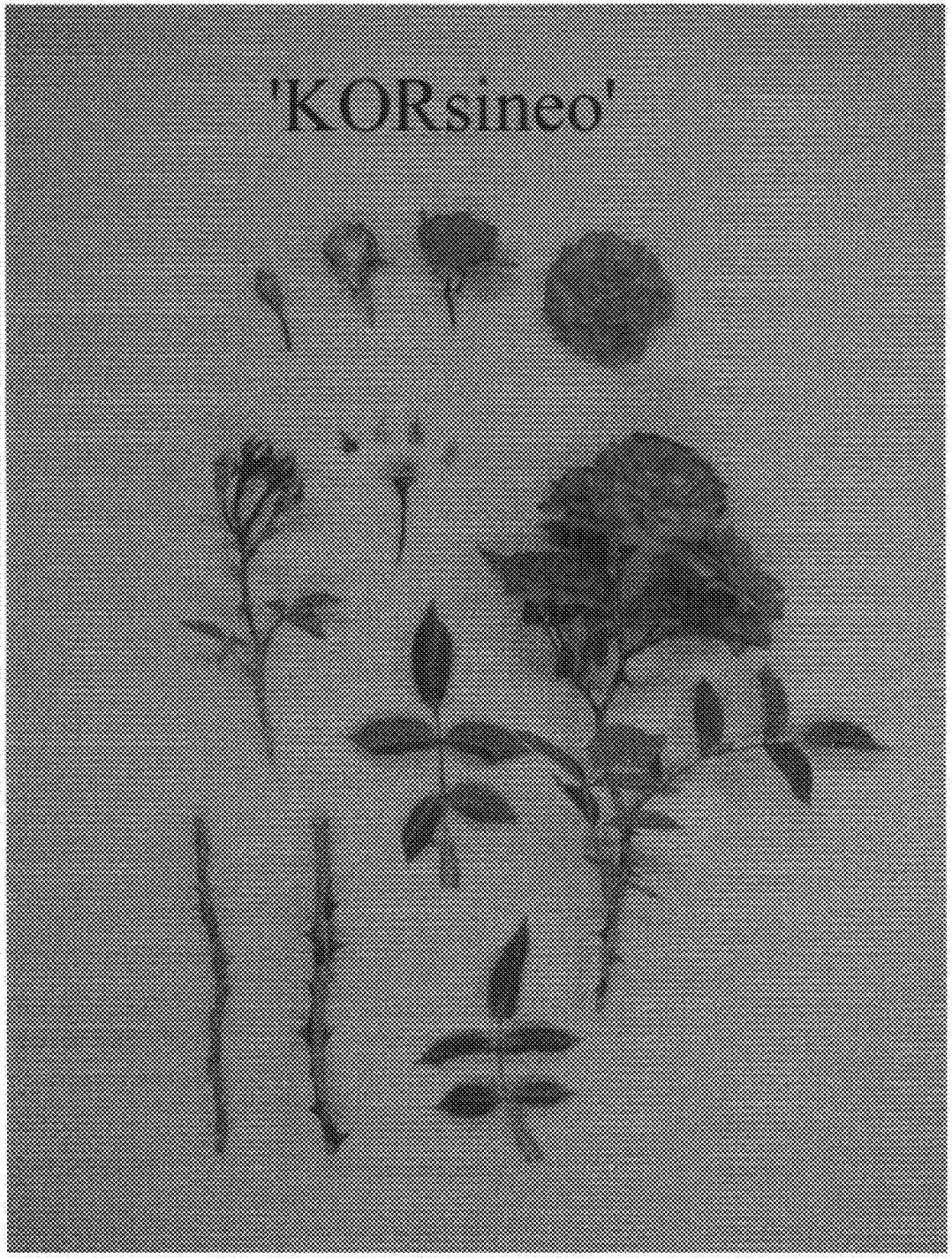
'KORsineo'